United States Patent [19]

Hasegawa

[11] Patent Number: 4,880,887

[45] Date of Patent: Nov. 14, 1989

[54] METHOD FOR CURING DENTAL RESINS

[75] Inventor: Akira Hasegawa, Inuyama, Japan

[73] Assignee: G-C Toshi Kogyo Corporation, Kasugai, Japan

[21] Appl. No.: 163,791

[22] Filed: Mar. 3, 1988

[30] Foreign Application Priority Data

Mar. 6, 1987 [JP] Japan .................................. 62-50295

[51] Int. Cl.$^4$ ....................... C08L 33/04; C08L 33/10
[52] U.S. Cl. .................................. 526/141; 525/248; 525/249; 525/250; 525/256; 525/257; 526/192; 526/204; 526/329.7; 523/109
[58] Field of Search ................ 523/109; 525/256, 257, 525/248, 249, 250; 526/141, 192, 204, 329.7

[56] References Cited

U.S. PATENT DOCUMENTS

| | | | |
|---|---|---|---|
| 4,182,035 | 1/1980 | Yamauchi et al. | 523/116 |
| 4,259,875 | 3/1981 | Yamauchi et al. | 528/956 |
| 4,259,917 | 3/1981 | Yamauchi et al. | 528/950 |
| 4,302,381 | 11/1981 | Omura et al. | 523/118 |

*Primary Examiner*—Allan M. Lieberman
*Attorney, Agent, or Firm*—Oblon, Spivak, McClelland, Maier & Neustadt

[57] ABSTRACT

In curing dental resins, polymerizable compounds having at least one ethylenically unsaturated double bond, such as mono- or poly-functional acrylates or methacrylates are polymerized in the presence of N-cyclohexy-5-ethylpyrimidinetrione, a specific organometallic compound typically including acetylacetone copper or lithium acetate, and an organohalogen compound. The amounts of the ethylpyrimidinetrione, organometallic and organohalogen compounds used are respectively 0.1 to 10 parts by weight, 0.001 to 0.2 parts by weight and 0.1 to 5 parts by weight with respect to the polymerization compounds.

6 Claims, 1 Drawing Sheet

METHOD FOR CURING DENTAL RESINS

BACKGROUND OF THE INVENTION

1. Field of the Invention

The present invention relates to a method for curing dental resins for the purpose of obtaining dental normal-temperature polymerizable resins, which are remarkably improved in terms of transparency, color stability and physical properties.

2. Statement of the Invention

About fifty years ago, that is in 1936, that one started to use polymethyl methacrylate mainly in dentistry and stomatoplasaty. Representative of synthetic resins resulting from the polymerization of polymerizable compounds having ethylenically unsaturated double bonds is polymetyl methacrylate. The application of methyl methacrylate and polymethyl methacrylate to dentistry has had its origin in the invention of the powder/liquid blending technique established in 1936. This technique has the advantage that the reactive catalyst can be supplied in two portions, viz., a powder portion and a liquid portion.

In general, the polymerization of methyl methacrylate is broken down into thermal polymerization and normal-temperature polymerization. The thermal polymerization involves the activation of peroxides by heat, and gives polymers through a succession of reactions of initiation, growth and interruption. In the normal-temperature polymerization, on the other hand, the action of promotors becomes important rather than the action of heat. The promotors, which were discovered in 1941 for the first time, have been used up to date and little improvement has been made since. Among others, the combination of dimethyl p-toluidine that is an aromatic tertiary amine with benzoyl peroxide that is an organic peroxide is found to be of the most general-purpose properties. However, this combination has the following grave disadvantages.

The first disadvantage is that the reaction product remaining in the cured synthetic resin turns yellow upon exposure to light.

The second is thata discoloration or coloration of the cured product occurs due to contacting sputum or exposure to the mouth temperature or in the intramouth environment including food refuses.

The third is that unreacted part of the promotor and derivatives not formed in the chainlike molecules act together as a plasticizer which causes a lowering of the physical properties of the polymerized synthetic resin.

The fourth is that the heat of polymerization is high.

The fifth is that the cured product is deficient in transparency.

The first disadvantage may be eliminated to some extent by the addition of an ultraviolet absorber. Not until now, however, is the second disadvantage practically overcome. What is more, the second disadvantage involves the coloration of the cured product which is originally caused by the inherent properties of the promotor and the so-called discoloration that is a gradual change in color. In an effort to overcome the third disadvantage, the plasticizer effect of the residual promotor is improved by making use of various types of polymers, in particular, methyl ester polymers in an increased amount. However, such an effort has still its own limit.

For normal-temperature polymerizable resins for dental purposes, certain combinations of benzoyl peroxide with aromatic tertiary amines have generally been used as catalysts. However, the obtained dental resins are poor in color stability and, in particular, suffer from noticeable yellowing. For instance, when the oral cavity restoration material obtained by this method is inserted into the mouth of a paatient, it has to be adjusted to a color as natural as her or his intramouth environment with much effort. Nonetheless, yellowing is initiated within a short period of time with the result that the restoration material assumes a quite unnatural color and loses aesthetic properties. Further, the so-called plasticizer effect of the residual promotor causes a lowering of the physical properties of the restoration material due to large amounts of the unreacted benzoyl peroxide or aromatic tertiary amines remaining therein. The fourth defect is that when the polymerizable compounds having at least one ethylenically unsaturated double bond are polymerized into a rebasing material applied directly in the mouth in the presence of the conventional catalyst, viz., a benzoyl peroxide/aromatic tertiary amine combination, the polymerized or cured product causes irritative pain to the mouth of a patient because of a large amount of heat generated during polymerization. The fifth defect, insufficient transparency of the cured product, remains substantially unsolved.

SUMMARY OF THE INVENTION

The present invention has been accomplished to eliminate various disadvantages of the prior art normal-temperature resin polymerization, i.e., insufficient transparency of cured products, changes-with-time of cured products under various oral conditions, yellowing of cured products due to the color inherent in the catalyst used, discoloration or coloration of cured products in the mouth, lowerings of the physical properties of cured products due to the plasticizer effect of the residual promotor, and irritative pain to the mouth of a patient due to a large amount of heat generated during polymerization.

As a result of intensive and extensive studies made to eliminate the aforesaid disadvantages of the existing polymerized products, it has been found that they are substantially eliminated by a method for curing dental resins characterized in that polymerizable compounds having at least one ethylenically saturated double bond are polymerized in the prosence of N-cyclohexyl-5-ethylpyrimidinetrione, an organometallic compound and an organohalogen compound.

DETAILED DESCRIPTION OF THE INVENTION

To achieve a remarkable effect according to the present invention, N-cyclohexyl-5-ethylpyrimidinetrione is specifically selected from numerous pyrimidinetrione derivatives. Besides N-cyclohexyl-5-ehtylpyrimidinetrione, the pyrimidinetrione derivaatives are generally known to include N-benzyl-5-phenylpyrimidinetrione, 5-butylpyrimidinetrione, 5-phenylpyrimidinetrione, 5,5-diethylpyrimidinetrione, 1,3,5-trimethylpyrimidinetrione, 2,4,6-(1H, 3H, 5H)pyrimidinetrione and 1,3-dimethylpyrimidinetrione. When polymerizing polymerizable compounds having at least one ethylenically unsaturated double bond for the preparation of mouth restoration materials, however, they cannot be used due to the following demerits. In other words, the use of N-benzyl-5-phenylpyrimidinetrione, 5-butylpyrimidinetrione or 1,3,5-trimethylpyrimidinetrione results in clouding of the cured products. Also, such pyrimidinetrione compounds cannot possibly be used in applications where quick-curing properties are required, since they retard curing. 5-phenylpyrimidinetrione or 5-ethylpyrimidinetrione cannot be used at all, since they require a curing period of about 1 day at room temperaature. 1,3-dimethylpyrimidinetrione also cannot be used at all, since it requires a curing period of about 1 day and, moreover, causes the cured product to turn reddish brown. 5,5-diethylpyrimidinetrione or 2,4,6-(1H, 3H, 5H)pyrimidinetrione have been found to have no catalytic effect whatsoever.

It has been found, however, that when N-cyclohexyl-5-ethylpyrimidinetrione is used for the polymerization of polymerizable compounds having at least one ethylenically unsaturated double bond, a curing time within 6 minutes 30 seconds or quick-curing properties cannot only be achieved, but the cured products are also as transparent as glass. In short, since the cured products are as transparent as glass, they can be colored with any color. In addition, the cured products undergo neither coloration nor discoloration in the mouth, and have by far improved physical properties. The polymer products obtained as the direct rebasing material by the polymerization of polymerizable compounds having at least one ethylenically unsaturated double bond with N-cyclohexyl-5-ethylpyrimidinetrione specified in the present invention have been found to be advantageous over those obtained with the conventional combinations of benzoyl peroxide with aromatic tertiary amines in that when the heat of polymerization is measured in a powder/liquid blending ratio of 2 g to 1 g, it decreases by abou 8° C in terms of temperature at the time of polymerization. This means that it is possible to considerably reduce the mouth irritation of heat.

The amount of N-cyclohexyl-5-ethylpyrimidinetrione added should preferably be in a range of 0.1 to 10 parts by weight with respect to polymerizable compounds having at least one ethylenically unsaturated double bond. In an amount of the pyrimidinetrione derivative departing from that range, it retards curing, and cannot be used for dental normal-temperataure polymerizable resins required to possess quick-curing properties.

In view of chemical morphology, the "polymerizable compounds having at least one ethylenically unsaturated double bond" in the present invention refer to monomers and prepolymers (i.e., dimers, trimers and other oligomers) as well as mixtures and copolymers thereof.

Examples of the monomers having at least one ethylenically unsaturated double bond may include methyl, ethyl, isopropyl, hydroxyethyl, tetrafurfuryl and glycidyl acrylaates and methacrylates; and examples of the monomers having two ethylenically unsaturated double bonds aromatic ones such as 2,2-bis(acryloxy or methacryloxyphenyl)propane, 2,2-bis[4-(2-hydroxy-3-acryloxy or methacryloxyphenyl]propane, 2,2-bis(4-acryloxy or methacryloxyethoxyphenyl)propane and 2,2-bis(4-acryloxy or methacryloxypropoxyphenyl)propane and aliphatic ones such as ethylene glycol, diethylene glycol, triethylene glycol, butylene glycol, neopentyl glycol, 1,3-butanedio, 1,4-buntanediol and 1,6-hexanediol diacrylate and dimethyacrylate. Examples of the monomers having three ethylenically unsaturated double bonds may include trimethylolpropane, trimethylolethane, pentaerythritol and trimethylolmethane acrylates and methacrylates; and examples of the m mers having four ethylenically unsaturated d( bonds may include pentaerythritol tetra-methacr and acrylate and others.

The organometallic compounds used may in( acetylacetone copper, copper acetate, copper o acetylacetone manganese, manganese naphthenate. tylacetone lithium, lithium acetate, acetylacetone zinc naphthenate, acetylacetone nickel, nickel ac( acetylacetone aluminium, acetylacetone calcium, tylacetone chromium (III), acetylacetone iron sodium naphthenate and rare earth octoate. These pounds may be used alone or in combination.

The amount of these organometallic compour compounds used should preferably be in a rang 0.001 to 0.2 parts by weight with respect to 100 par weight of the polymerizable compounds having at one ethylenically unsaturated double bond. I amount of below 0.001 part by weight, the reucti reactivity makes it impossible to obtain any quick ing normal-temperataure polymerizable resins for tal purposes. In an amount of greater than 0.2 par weight, on the other hand, colors chaaracteristic c organometallic compounds are developed. Fo stance, acetylacetone copper and iron (III) show a color and a reddish brown color, respectively.

The organohalogen compounds used may in( dilauryldimethylammonium chloride, lauryldime benzylammonium chloride, benzyltrimethylammo chloride, diisobutylamine hydrochloride, tet butylammonium chloride, triethylamine hydrochlc trimethylamine hydrochloride, dimethylamine h} chloride, dieithylamine hydrochloride, methyla hydrochloride, ethylaamine hydrochloride, isobu mine hydrochloride, triethanolamine hydrochlc β-phenylethylamine hydrochloride, acetylcholine ( ride, 2-chlorotriethylamine hydrochloride, (2-chlc thyl)trimethylammonium chloride, tetra-decylc thylbenzylammonium chloride, tetraethylammo chloride, tetramethylammonium chloride, rabutylammonium bromide, benzylriethylammo bromide, benzyltrimethylammonium bromide, rabutylammonium fluoride and tetrabutylammo iodide. These compounds may be used alone or in bination. Of these organohalogen compounds, pr ence is given to the three compounds, i.e., dilaurylc thylammonium chloride, lauryldimethylbenzy monium chloride and tetra-n-butylammonium chlo since they are soluble in the polymerizable compo having at least one ethylenically unsaturated dc bond in an amaount of about 5 parts by weight at mal temperature. However, other organohalogen ( pounds should be filtered for practical use, since solubility is very low at normal temperature.

The amount of these organohalogen compoun compounds used should preferably be in a range o to 5 parts by weight with respect to 100 parts by w( of the polymerizable compounds having at least ethylenically unsaturated double bond. In an amou below 0.1 part by weight, the reduction in react makes it impossible to obtain any quick-curing nor temperature polymerizable resins for dental purp In an amount of greater than 5 parts by weight, o: other hand, the curing time is kept constant but, r theless, the quality required for rebasing material plied directly in the mouth is not satisfied due t creases in the amount of heat generated at the tin polymerization. Besides, colors characteristic of the organohalogen compounds are developed.

By way of example, dilauryldimethylammonium chloride shows a light yellow color. Hence, any colorless, transparent cured product is by no means obtained.

Fillers may be used for the purpose of improving the physical properties of polymers. To this end, inorganic and/or organic fillers may be used, including, for instance, quartz powders, alumina powders, glass powders, kaolin, talc, calcium carbonate, barium aluminosilicate glass, titanium oxide, borosiliccate glass, colloidal silica powders, so-called organic composite fillers obtained by compacting colloidal silica with a polymer and pulverizing the compact, alumina whiskers, beryllium oxide whiskers, boron carbonate whiskers, silicon carbide whiskers, silicon nitride whiskers and various metal whiskers (chromium, copper, iron, nickel). As the polymer powders, use may be made of powdered methyl polyacrylate, methyl polymethacrylate, ethyl polymethacrylate, methyl methacrylate-ethyl methacrylate copolymers, crosslinked type methyl polymethacrylate, ethylene-vinyl acetate copolymers, styrene-butadiene copolymers, acrylonitrile-styrene copolymers and acrylonitrile-styrene-butadiene copolymers. Alternatively, these polymer powders may be mixed with the aforesaid inorganic powders or organic composite fillers.

Before mixing with a binder resin, the aforesaid inorganic fillers may preferably be treated with a coupling agent capable of reacting with both the filler and binder resin. The coupling agents used may include organofunctional silane coupling agents, titanate coupling agents and aluminate coupling agents. Alternatively, the inorganic fillers may be grafted on the surfaces for bonding to the binder resin.

The organofunctional silane coupling agents used may include $\gamma$-methacryloxypropyl trimethoxy silane, vinyltrichlorosilane, vinyltris($\beta$-methoxyetholxy)silane, $\beta$-mehacryloxypropyl methyldimethoxy silane, $\beta$-glycidoxypropyl trimethoxy silane, $\beta$-chloropropyl trimethoxy silane, $\beta$-(3,4-epoxycyclohexyl)ethyl trimethoxy silane, trimethylchlorosilalne, dimethyldichlorosilane, hexamethyldisilane, $\gamma$-aminopropyl triethoxy silane, N-$\beta$-(aminoethoxy)-$\gamma$-aminopropyl trimethoxy silane and $\gamma$-ureidopropyl trimethoxy silane.

Any suitable but not exclusive methods may be used for the surface treatment with these coupling agents. Although varying with the properties demanded and not generally determined, the amount of the coupling agents used may preferably be selected from a range c 0.1 to 20 parts by weight, particularly 1 to 10 parts b weight with respect to inorganics.

EXAMPLES

The Examples of the present invention and for Com parison Examples will be given below. It is understoo however, that the present invention is not exclusivel limited to the examples.

Examples 1 to 10 and 12 to 16 demonstrate the curin of methyl methacrylate, that is representative of th monomer having one ethylenically unsaturated doubl bond, with the combinaations of N-cyclohexyl-5-ethyl pyrimidinetrione, organometallic compounds and or ganohalogen compounds specified in the present inven tion. Example 11, the curing of ethyl methacrylate, an Example 17, the curing of 2,2-bis[4-(2-hydroxy-3 methacryloxyphenyl)]propane and neopenptyl glycc dimethacrylate. In Comparison Example 1, the conven tional combination of benzoyl peroxide with dimethy p-toluidine was applied for curing. In Comparison Ex amples 2 and 3, two pyrimidinetrione derivatives othe than N-cyclohexyl-5-ethylpyrimidinetrione was applie for curing. In Comparison Examples 4 to 9, the amount of N-cyclohexyl-5-ethylpyrimidinetrione, the organc metallic compound (acetylacetone copper) and the or ganohalogen compound (dilauryldimethylammoniun chloride) applied departed from the respective pre ferred ranges.

Testing methods and items are set out in Table 1 an FIGS. 1 to 3, and the results of testings are shown i Table 2.

TABLE 1

Figure 1:
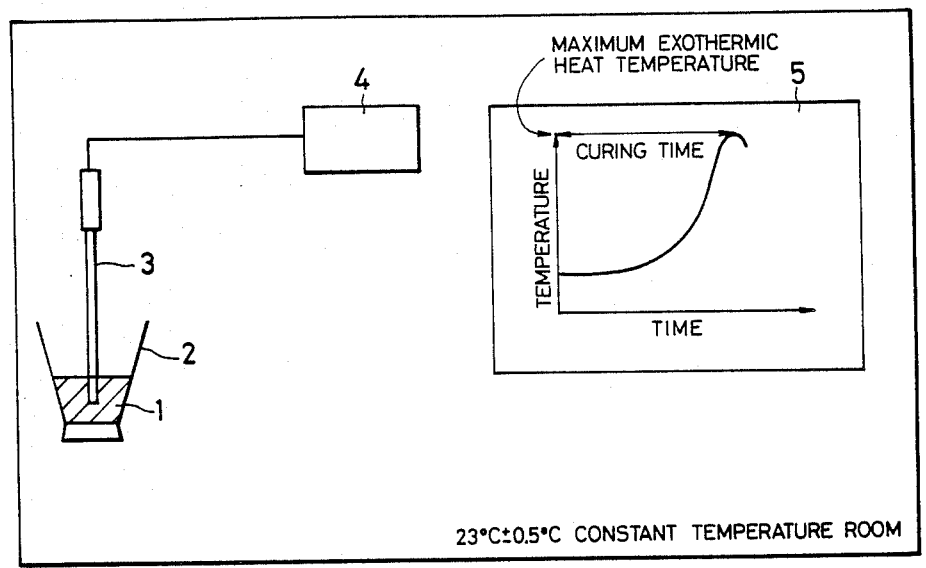
FIG. 1 is illustrative of the testing methods for curin time and maximum exothermic heat temperature wit reference numeral 1 denoting a powder/liquid mixture 2, a silicone rubber cup, 3, a thermistor thermometer, 4 an amplifier and 5, a recorder for recording the relation ship between the temperature and the time to displa the curing time and the maximum exothermic heat tem perature.
Figure 2:
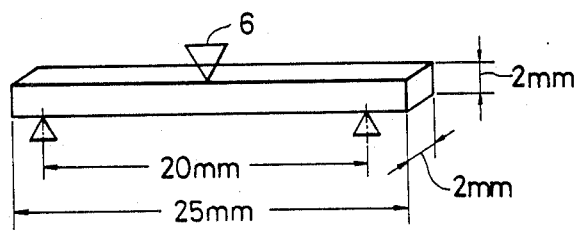
FIG. 2 illustrates the method for bending strengt testing according to ISO 4049 with reference numeral standing for a cross head working at a cross head spee of 1.0 mm/min.
Figure 3A:
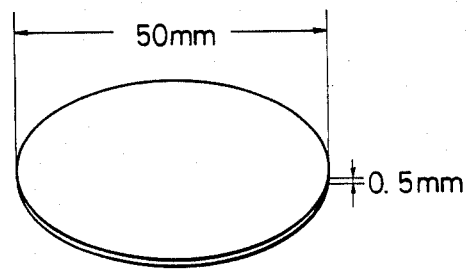
FIGS. 3(A) and (B) illustrates the methods for wate absorption according to A.D.A. Nos. 13 and 27, respec tively.
Figure 3B:
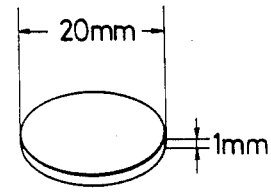

| Items | Testing Environment | Testing Items and Methods | | Remarks | Figures for Reference |
|---|---|---|---|---|---|
| | | Amount of Powder-Liquid Mixed | Measuring Methods | | |
| Transparency | Room Environment | Powder: 2 g Liquid: 1 g | Visual Observation | $20\phi \times 3$hmm | |
| Color of Cured Products | Room Environment | Powder: 2 g Liquid: 1 g | Visual Observation | $20\phi \times 3$hmm | |
| Curing Time (min. sec.) | 23° C. ± 0.5° C. | Powder: 2 g Liquid: 1 g | Exothermic process with thermistor thermometer | | FIG. 1 |
| Bending Strength (Kg/cm$^2$) | Room Temperature | Powder: 2 g Liquid: 1 g | ISO 4049 (Three-point bending) | Cross Head Speed 1 mm/min 25 × 2 × 2 mm size | FIG. 2 |
| Knoop Hardness | 23° C. ± 0.5° C. | Powder: 2 g Liquid: 1 g | 15 g, 30 sec. Shimazu Knoop Hardness Meter | | |
| Water Absorption (mg/cm$^2$) | Room Temperature | Powder: 2 g Liquid: 1 g | ADA No. 13 (ADA No. 27 applied Example 17) | ADA No. 13 $50\phi \times 0.5$ h mm ADA No. 27 $20\phi \times 1$ h mm | FIG 3(A) FIG. 3(B) |

TABLE 1-continued

| Items | Testing Environment | Amount of Powder-Liquid Mixed | Measuring Methods | Remarks | Figures for Reference |
|---|---|---|---|---|---|
| | | Testing Items and Methods | | | |
| Maximum Endothermic Heat Temperature | 23° C. ± 0.5° C. | Powder: 2 g Liquid: 1 g | Exothermic heat measurement with thermistor thermometer | | FIG. 1 |

EXAMPLE 1

| Powder Components | p.b.w. |
|---|---|
| Methyl/ethyl copolymer | 200 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 2

| Powder Components | p.b.w. |
|---|---|
| Methyl/ethyl copolymer | 160 |
| Organic composite filler | 40 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 3

| Powder Components | p.b.w. |
|---|---|
| Methyl/ethyl copolymer | 160 |
| Crosslinked polymer | 40 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 4

| Powder Components | p.b.w. |
|---|---|
| Methyl/ethyl copolymer | 200 |
| N—cyclohexyl-5-ethylpyrimidinetrione | 0.1 |
| Acetylacetone copper | 0.002 |
| Liquid Components | p.b.w. |
| Methyl methacrylate | 9.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 5

| Powder Components | p.b.w. |
|---|---|
| Methyl/ethyl copolymer | 200 |
| N—cyclohexyl-5-ethylpyrimidinetrione | 6 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 6

| Powder Components | p.b.w. |
|---|---|
| Methyl/ethyl copolymer | 200 |
| N—cyclohexyl-5-ethylpyrimidinetrione | 2 |
| Acetylacetone copper | 0.001 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

EXAMPLE 7

| Powder Components | p.b.w. |
|---|---|
| Methyl/ethyl copolymer | 200 |
| N—cyclohexyl-5-ethylpyrimidinetrione | 2 |
| Acetylacetone copper | 0.2 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 8

| Powder Components | p.b.w. |
|---|---|
| Methyl/ethyl copolymer | 200 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 9

| Powder Components | p.b.w. |
|---|---|
| Methyl/ethyl copolymer | 200 |

-continued

| | |
|---|---|
| N—cyclohexyl-5-ethylpyrimidinetrione | 2 |
| Lithium acetate | 0.01 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 10

| Powder Components | p.b.w. |
|---|---|
| Methyl/ethyl copolymer | 200 |
| N—cyclohexyl-5-ethylpyrimidinetrione | 2 |
| Acetylacetone copper | 0.002 |
| Liquid Components | p.b.w. |
| Methyl methacrylate | 100 |
| Dilauryldimethylammonium chloride | 2 |
| Butyl hydroxytoluene | 0.03 |
| U. V. absorber | 0.5 |

EXAMPLE 11

| Powder Components | p.b.w. |
|---|---|
| Methyl/ethyl copolymer | 200 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 12

| Powder Components | p.b.w. |
|---|---|
| Polymethyl methacrylate | 200 |
| N—cyclohexyl-5-ethylpyrimidinetrione | 2 |
| Acetylacetone copper | 0.002 |
| Liquid Components | p.b.w. |
| Methyl methacrylate | 99.9 |
| Ethylene glycol dimethacrylate | 0.1 |
| Dilauryldimethylammonium chloride | 1 |
| Butyl hydroxytoluene | 0.03 |
| U. V. absorber | 0.5 |

EXAMPLE 13

| | p.b.w. |
|---|---|
| Powder Components | |
| Methyl/ethyl copolymer | 200 |
| N—cyclohexyl-5-ethylpyrimidinetrione | 8 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

EXAMPLE 14

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.1 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

EXAMPLE 15

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 0.2 |
| Butyl hydroxytoluene | 0.03 |
| U.V. absorber | 0.5 |

EXAMPLE 16

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 5 |
| Butyl hydroxytoluene | 0.03 |
| U.V. absorber | 0.5 |

EXAMPLE 17

| | p.b.w. |
|---|---|
| Powder Components | |
| Glass powders | 120 |
| Colloidal silica powders | 80 |
| N—cyclohexyl-5-ethylpyrimidinetrione | 2 |
| Acetylacetone copper | 0.002 |
| (surface-treated with τ-methcryloxpropyl trimethoxy silane) | |
| Liquid Components | |
| 2,2-bis{4-(2-hydroxy-3-methacryloxyphenyl)] propane | 60 |
| Neopentyl glycol dimethacrylate | 40 |
| Dilauryldimethylammonium chloride | 1 |
| Butyl hydroxytoluene | 0.03 |
| U.V. absorber | 0.5 |

COMPARISON EXAMPLE 1

Formulation

| | p.b.w. |
|---|---|
| Powder Components | |

-continued

| | p.b.w. |
|---|---|
| Metyl/ethyl copolymer | 200 |
| B.P.O. | 2 |
| Liquid Components | |
| Methyl methacrylate | 99.9 |
| Ethylene glycol dimethacrylate | 0.1 |
| Dimethyl p-toluidine | 1 |
| Butyl hydroxytoluene | 0.03 |
| U.V. absorber | 0.5 |

COMPARISON EXAMPLE 2

| | p.b.w. |
|---|---|
| Powder Components | |
| Methyl/ethyl copolymer | 200 |
| N—benzyl-5-phenylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 3

Formulation

| | p.b.w. |
|---|---|
| Powder Components | |
| Methyl/ethyl copolymer | 200 |
| 5-buthylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 4

Formulation

| | p.b.w. |
|---|---|
| Powder Components | |
| Methyl/ethyl copolymer | 200 |
| N—cyclohexyl-5-ethylpyrimidinetrione | 0.05 |
| Acetylacetone | 0.002 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 5

Formulation

| | p.b.w. |
|---|---|
| Powder Components | |
| Methyl/ethyl copolymer | 200 |
| N—cyclohexyl-5-ethylpyrimidinetrione | 15 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 6

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.0004 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 7

| | p.b.w. |
|---|---|
| Powder Components | |
| Methyl/ethyl copolymer | 200 |
| N—cyclohexyl-5-ethylpyrimidinetrione | 2 |
| Acetylacetone copper | 1 |
| Liquid Components | |
| Methyl methacrylate | 99.9 |
| Ethylene glycol dimethacrylate | 0.1 |
| Dilauryldimethylammonium chloride | 1 |
| Butyl hydroxytoluene | 0.03 |
| U.V. absorber | 0.5 |

COMPARISON EXAMPLE 8

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 0.05 |
| Butyl hydroxytoluene | 0.03 |
| U.V. absorber | 0.5 |

COMPARISON EXAMPLE 9

| | p.b.w. |
|---|---|
| Powder Components | |
| Methyl/ethyl copolymer | 200 |
| N—cyclohexyl-5-ethylpyrimidinetrione | 2 |
| Acetylacetone copper | 0.002 |
| Liquid Components | |
| Methyl methacrylate | 99.9 |
| Ethylene glycol dimethacrylate | 0.1 |
| Dilauryldimethylammonium chloride | 10 |
| Butyl hydroxytoluene | 0.03 |
| U.V. absorber | 0.5 |

TABLE 2
Results of Testings

| | Transparency | Color of Cured Products | Curing Time (min. sec.) | Bending Strength (kg/cm$^2$) | Knoop Hardness | Water Absorption (kg/cm$^2$) | Maximum Endothermic Heat Temperature (C.°) |
| --- | --- | --- | --- | --- | --- | --- | --- |
| Example 1 | Excellent | Colorless | 3'25" | 914 (58) | 10.1 | 0.37 | 65 |
| Example 2 | Excellent | Colorless | 4'00" | 843 (19) | 13.9 | 0.27 | 68 |
| Example 3 | Excellent | Colorless | 3'55" | 937 (42) | 11.9 | 0.24 | 68 |
| Example 4 | Excellent | Colorless | 5'30" | 832 (28) | 10.8 | 0.35 | 60 |
| Example 5 | Excellent | Colorless | 4'40" | 925 (8) | 11.1 | 0.38 | 63 |
| Example 6 | Excellent | Colorless | 4'15" | 813 (24) | 11.0 | 0.37 | 66 |
| Example 7 | Excellent | Colorless | 4'00" | 904 (11) | 11.2 | 0.37 | 63 |
| Example 8 | Excellent | Colorless | 4'15" | 851 (10) | 10.8 | 0.35 | 69 |
| Example 9 | Excellent | Colorless | 5'45" | 821 (52) | 10.8 | 0.35 | 61 |
| Example 10 | Excellent | Colorless | 3'20" | 883 (18) | 10.2 | 0.33 | 65 |
| Example 11 | Excellent | Colorless | 1'05" | 820 (21) | 10.2 | 0.38 | 70 |
| Example 12 | Excellent | Colorless | 6'30" | 1015 (63) | 13.0 | 0.29 | 59 |
| Example 13 | Excellent | Colorless | 4'45" | 903 (20) | 10.8 | 0.35 | 64 |
| Example 14 | Excellent | Colorless | 3'25" | 897 (54) | 11.1 | 0.35 | 68 |
| Example 15 | Excellent | Colorless | 5'05" | 869 (12) | 10.6 | 0.29 | 68 |
| Example 16 | Excellent | Colorless | 4'50" | 911 (6) | 11.8 | 0.30 | 68 |
| Example 17 | Good | Colorless | 2'30" | 1455 (108) | 68.5 | 0.64 | 39 |
| Comparative Example 1 | Bad | Yellow | 5'00" | 787 (51) | 10.1 | 0.35 | 77 |
| Comparative Example 2 | Bad | Clouded | 7'45" | 744 (60) | 10.5 | 0.44 | 67 |
| Comparative Example 3 | Bad | Clouded | 7'30" | 677 (45) | 10.2 | 0.48 | 69 |
| Comparative Example 4 | Excellent | Colorless | 15'15" | 788 (85) | 11.6 | 0.38 | 60 |
| Comparative Example 5 | Excellent | Colorless | 11'20" | 808 (11) | 10.1 | 0.40 | 66 |
| Comparative Example 6 | Excellent | Colorless | 10'45" | 704 (29) | 9.8 | 0.39 | 62 |
| Comparative Example 7 | Excellent | Light Blue | 3'45" | 866 (10) | 11.8 | 0.38 | 63 |
| Comparative Example 8 | Excellent | Colorless | 27'25" | 611 (32) | 9.5 | 0.44 | 65 |
| Comparative Example 9 | Good | Yellow | 4'00" | 820 (38) | 10.5 | 0.31 | 72 |

The bracketed figures are the standard deviation.
Knoop hardness and water absorption are given by averaged values of two measurements.
Water absorption in Example 17 was measured according to ADA No. 27.

In Examples 1 to 16, the cured products become colorless and transparent. In Example 17, the cured product containing the inorganic filler as an additional component is colorless, and shows satisfactory transparency, although slightly inferior in that point to the cured products of Examples 1 to 16. However, the cured product of Example 17 is higher than other cured products in Knoop hardness, and exhibits a much higher bending strength. The cured product of Example 2 is improved in Knoop hardness because of the presence of the organic composite filler, while the cured product of Example 3 is enhanced in bending strength because of the presence of the crosslinked polymer. Example 4 is an example in which the amount of N-cyclohexyl-5-ethylpyrimidinetrione added is smaller, while Examples 5 and 13 are examples in which that amount is larger. The products of these examples tend to have a slightly prolonged curing time. Example 6 is an example in which the amount of acetylacetone copper added is smaller. In a quantity below that amount, a cursing time is prolonged, as in Comparison Example 6. Examples 7 and 14 are examples in which the amount of acetylacetone copper added is larger. In a quantity greater than that amount, a light blue color characteristic of acetylacetone copper is developed, as in Comparison Example 7. Example 8 is an example in which lauryldimethylbenzylammonium chloride is used in place of dilauryldimethylammonium chloride but in the same amount. The product of this example is slightly longer in the length of curing time than that of Example 1. Example 9 is an example in which lithium acetate is used in place of acetylacetone copper but in the same amount. The product of this example is longer in the length of curing time that that of Example 1. Example 10 is an example in which methyl methacrylate is independently used as the polymerizable compounds having at least one ethylenically unsaturated double bond. A colorless and transparent cured product is obtained, as is the case with the addition of ethylene glycol dimethacrylate. Example 11 is an example in which ethyl methacrylate is used as the polymerizable compounds having at least one ethylenically unsaturated double bond. A colorless and transparent cured product is obtained, as in the case with the addition of methyl methacrylate. Example 12 is an example in which polymethyl methacrylate is used as one powder component. The product of this example cures at a slightly slow rate, but gives a colorless and transparent cured mass. In Examples 15 and 16, the amount of dilauryldimethylammonium chloride added is decreased and increased, respectively. Although varying slightly in the length of curing time, the products are not at all affected in terms of other properties.

EFFECTS OF THE INVENTION

The present invention provides a method for curing dental resins characterized in that the polymerizable compounds having at least one ethylenically unsaturated double bond are polymerized using N-cyclohexyl- 5-ethylpyrimidinetrione as the polymerization initiator and various organometallic and organohalogen compounds as the polymerization promotor. With the polymerization method of the present invention, it is possible to obtain cured products which do never suffer from yellowing, and are superior in transparency to those obtained by the polymerization relying upon the conventionally employed organic peroxide/aromatic tertiary amine combinations. The resulting cured products have by far improved physical properties without discoloration in the intramouth cavity. When it is intended to polymerize the polymerizable compounds having at least one ethylenically unsaturated double bond with pyrimidinetrione derivatives other than N-cyclohexyl-5-ethylpyrimidinetrione, it is found that some of the compounds do not initiate polymerization, or are only polymerized at an extremely slow rate unsuitable for dental normal-temperature resins. Another compounds may be polymerized, but the resulting cured products are too clouded to be suitable for dental purposes.

Further, the products cured by the polymerization using as the initiator N-cyclohexyl-5-ethylpyrimidinetrione are superior in physical properties to those obtained by the polymerization using the organic peroxide/aromatic tertiary amine combinations and other pyrimidinetrione derivatives When the polymerizable compounds having at least one ethylenically unsaturated double bond are applied directly as the rebasing material in the mouth, to use N-cyclohexyl-5-ethylpyrimidinetrione as the initiator has an effect of alleviating the irritation of the patient's mouth, since the amount of heat generated during polymerization is smaller than that generated when using the organic peroxide/aromatic tertiary amine combination.

What is claimed is:

1. A method for curing a polymerizable dental compound, wherein the dental compound comprises a polymerizable material having at leas one ethylenically unsaturated double bond, comprising:

polymerizing said dental compound in the presence of (1) N-cyclohexyl-5-ethylpyrimidinetrione in an amount of 0.1 to 10 parts by weight with respect to said dental compound, (2) at least one organometallic compound selected from the group consisting of acetylacetone copper, copper acetate, copper oleate, acetylacetone manganese, manganese naphthenate, manganese octylate, acetylacetone cobalt (III), cobalt naphthenate, acetylacetone lithium, lithium acetate, cetylacetone zinc, zinc naphthenate, acetylacetone nickel, nickel acetate, acetylacetone aluminum, acetylacetone calcium, cetylacetone chromium (III), acetylacetone iron (III), sodium naphtheate and rare earth octoate in an amount of 0.001 to 0.2 parts by weight with respect to said dental compound and (3) an organohalogen compound in an amount of 0.1 to 5 parts by weight with respect to said dental compound.

2. A method as defined in claim 1, wherein said polymerizable compound having at least one ethylenically unsaturated double bond is a monofunctional methacrylate.

3. A method as defined in claim 1, wherein said polymerizable compound having at least one ethylenically unsaturated double bond is a monofunctional acrylate.

4. A method as defined in claim 1, wherein said polymerizable compound having at least one ethylenically unsaturated double bond is a polyfunctional methacrylate.

5. A method as defined in claim 1, wherein said polymerizable compound having at least one ethylenically unsaturated doublel bond is a polyfunctional acrylate.

6. A method as defined in claim 1, wherein a filler is additinally incorporated.

* * * * *